United States Patent
Rodriguez et al.

(10) Patent No.: US 8,685,419 B2
(45) Date of Patent: Apr. 1, 2014

(54) COSMETIC COMPOSITION COMPRISING A COLORANT AND METHOD OF COSMETIC TREATMENT

(75) Inventors: Ivan Rodriguez, Cauffry (FR); Valerie Jeanne-Rose, Argenteuil (FR)

(73) Assignee: L'Oreal, Paris (FR)

( * ) Notice: Subject to any disclaimer, the term of this patent is extended or adjusted under 35 U.S.C. 154(b) by 0 days.

(21) Appl. No.: 12/809,175

(22) PCT Filed: Dec. 2, 2008

(86) PCT No.: PCT/FR2008/052173
§ 371 (c)(1),
(2), (4) Date: Oct. 18, 2010

(87) PCT Pub. No.: WO2009/080927
PCT Pub. Date: Jul. 2, 2009

(65) Prior Publication Data
US 2011/0033510 A1    Feb. 10, 2011

Related U.S. Application Data

(60) Provisional application No. 61/022,524, filed on Jan. 22, 2008.

(30) Foreign Application Priority Data

Dec. 20, 2007 (FR) ...................................... 07 60112

(51) Int. Cl.
*A61K 8/02* (2006.01)
*A61Q 19/00* (2006.01)

(52) U.S. Cl.
CPC ..................................... *A61Q 19/00* (2013.01)
USPC ......................................................... 424/401

(58) Field of Classification Search
None
See application file for complete search history.

(56) References Cited

U.S. PATENT DOCUMENTS

| | | | |
|---|---|---|---|
| 2003/0206879 A1* | 11/2003 | Glenn et al. | 424/70.12 |
| 2004/0011254 A1 | 1/2004 | Chianelli et al. | |
| 2005/0238611 A1* | 10/2005 | Rando et al. | 424/70.122 |
| 2007/0033747 A1* | 2/2007 | Chianelli et al. | 8/498 |
| 2008/0190324 A1* | 8/2008 | Chianelli et al. | 106/487 |
| 2009/0196894 A1* | 8/2009 | Ehlis et al. | 424/401 |

FOREIGN PATENT DOCUMENTS

JP    5 51537    3/1993

OTHER PUBLICATIONS

Machine Translation of JP05-51537 (retrieved online on Feb. 9, 2012).*
"Bonding in Benzene" Jim Clark, 2000 (pp. 1-6).*
"Bond Length" Wikipedia (downloaded on Jun. 15, 2012) pp. 1-4.*
"Indigo Dye" Wikipedia (downloaded on Jun. 15, 2012) pp. 1-4.*
Olphen Van, H. "Maya Blue: A Clay-Organic Pigment?" Science, vol. 154, XP 002440497, pp. 645-646 (Nov. 4, 1996).

* cited by examiner

*Primary Examiner* — Bethany Barham
(74) *Attorney, Agent, or Firm* — Oblon, Spivak, McClelland, Maier & Neustadt, L.L.P.

(57) ABSTRACT

The present invention relates to a cosmetic composition comprising, in a cosmetically acceptable medium, a colorant comprising an inorganic fibrous matrix with tunnels and organic dye compounds incorporated at least partially in said tunnels, said compounds being selected from the indigoids, and present in an amount such that the weight ratio of colorant to matrix is greater than or equal to 0.028.

The invention also relates to a method of cosmetic treatment of keratinous materials, comprising the application of said cosmetic composition.

18 Claims, No Drawings

COSMETIC COMPOSITION COMPRISING A COLORANT AND METHOD OF COSMETIC TREATMENT

The present invention relates to cosmetic compositions comprising novel colorants, as well as a method of cosmetic treatment using them.

Make-up compositions generally contain colorants, such as pigments or dyes, which endow the deposited make-up with the desired colours. The number of blue colorants usable in cosmetics is particularly limited. Those known are mainly mineral pigments or dyes such as Prussian blue or ultramarine, and organic pigments or dyes such as phthalocyanine blue, patent blue (acid blue) and indigo. The organic colorants have greater colouring power than the mineral colorants, which means that their use is preferred to that of the mineral colorants.

However, it was found that said organic colorants tended to discolour when they were exposed to UV, which is not the case with the mineral colorants, which display good stability on exposure to UV.

In order to correct these problems of UV stability, it was proposed to photostabilize organic dyes, by adding UV absorbents or antioxidants, notably by Daniela Cristea, Gerard Vilarem in Dyes and Pigments 70 (2006) p 238-245. However, these additives do not permit long-term stabilization of colour, i.e. for several months; moreover, the presence of certain additives in cosmetic compositions may be undesirable, depending on the nature of these additives, or may give rise to formulation problems, such as lack of stability, incompatibility with other components, etc.

The aim of the present invention is to propose novel organic colorants, which can be used in cosmetics and have good UV stability, lasting for several months.

Thus, the present invention relates to a cosmetic composition, comprising, in a cosmetically acceptable medium, at least one colorant comprising an inorganic fibrous matrix with tunnels and at least one organic dye compound incorporated at least partially in said tunnels, in which said organic dye compound is selected from the indigoids, and is present in the colorant in an amount such that the weight ratio of initial organic dye compound to inorganic fibrous matrix is greater than or equal to 0.028 (i.e. 2.8%).

The colorants according to the invention can have a very varied range of colour, in the blue domain, ranging from blue to blue-green, via deep blue, turquoise blue or indigo blue, which makes it possible to use them particularly advantageously in cosmetic compositions, notably for make-up.

This is particularly remarkable and advantageous since these colorants have an almost identical basic composition, which makes it possible to simplify their application in cosmetic compositions, said colorants being interchangeable within one and the same basic composition, obviating the need to adapt each composition to the nature of each colorant.

The colorants according to the invention also offer the advantage that they do not bleed in the usual cosmetic media, whether they comprise carbon-containing oils or the usual silicone oils.

Colorants formed from indigo and clay are known in the prior art. We may notably mention the pigments known in the literature by the name 'Maya Blues' which result from the combination of indigo and a clay, which can be of the palygorskite or sepiolite type.

'Maya Blue' is a blue pigment found at several archaeological sites, notably in Mexico and in Guatemala. Notably it was found on the wall paintings at Chichen Itza (1931, Merwin) and Bonampak, in Mexico.

It is remarkable for its very particular blue colour as well as for its incredible resistance, which has allowed it to be found on walls, pottery, and religious objects, dating from the 16th century, in a very good state of preservation, despite the unfavourable, notably climatic, storage conditions.

Regarding synthetic pigments of the 'Maya Blue' type, we may notably mention U.S. Pat. No. 7,052,541, which describes colorants that can be used in the area of paints, plastics or cements, and which are obtained from a derivative of indigo and a clay, which can be fibrous or lamellar.

A particular method is also known, from US2006/0200917, for preparation of colorants intended for the area of paint or cement, consisting of mixing an indigo or a derivative of indigo, with a fibrous or lamellar clay, and then exposing the mixture to ultraviolet radiation, notably at a wavelength of 200-400 nm, for 1 minute to 48 hours.

However, none of these documents describes or suggests the use of such colorants in cosmetic compositions, notably for make-up, and even less the cosmetic use of the particular colorants such as described in the present invention.

Moreover, it is not mentioned at all in these documents that the colorants have good photostability.

The colorants according to the invention comprise an inorganic fibrous matrix with tunnels, and at least one organic dye compound incorporated at least partially in said tunnels.

"Partially" means that at least 30 wt. % of the total amount of organic dye is included in the channels of the fibrous matrix.

The incorporation of the organic dye in said organic matrix can notably be illustrated by NMR, notably by 2D HECTOR NMR at very high speed of rotation MAS of 29Si, 13C and 1H of the organic dye; we can thus determine the structure of the fibrous matrix and the presence of incorporated dye ('in' species) and of dye adsorbed on the surface ('out' species); by comparing the chemical shift of the 13C spectrum of the organic dye as such, with that of the organic dye in the final colorant, it is possible to characterize the incorporation of said dye in said matrix. Finally, the correlation observed between the protons of the organic dye and site 1 of the fibrous matrix in the 2D HECTOR 1H-29Si experiment offers tangible proof of inclusion of said dye in said matrix.

It was in fact found that with the methods according to the invention, it is possible to obtain colorants that are particularly photostable, said photostability notably being due in part to the fact that the organic dye compounds are at least partially incorporated in the tunnels of the fibrous matrix.

Said inorganic fibrous matrix with tunnels is preferably a clay.

It is known that clay is a sedimentary rock, largely composed of specific minerals, silicates generally of aluminium more or less hydrated, which have a lamellar structure or a fibrous structure. They are classified in three broad categories according to the thickness of the lamellae, which correspond to a number of layers of tetrahedral and octahedral oxides. The interstices between the lamellae can contain water as well as ions. As a result there are variations of the distance between lamellae, and therefore macroscopic dimensional variations of the clay when it is hydrated or it dries out.

The clays for use within the scope of the present invention are fibrous clays (or clays with fibrous structure), and notably such as sepiolite or palygorskite (also called attapulgite).

The palygorskites and the sepiolites are clays that are generally constituted of fibres of the order of 1 to 3 microns in length.

In sepiolite, each fibre is formed from a multitude of tunnels (or fine channels) of about 1 $nm^2$, regularly spaced. This particular configuration as elongated hollow bricks, in keeping with its crystalline arrangement, gives it a very large specific surface. The general formula used in the literature for its crystalline structure is $Mg_4Si_6O_5(OH)_2.6(H_2O)$ or more preferably $(Si)_{12}(Mg)_8(O)_{30}(OH)_4(OH_2)_4 \cdot 8H_2O$ Within the scope of the invention, it does not matter whether sepiolite or palygorskite is used, or even a mixture of sepiolite and palygorskite, in any proportions; and preferably sepiolite alone.

The organic dye compounds according to the invention are selected from the indigoids, alone or mixtures thereof.

Preferably, indigo is used as the organic dye compound; it is a natural dye, notably derived from the indigo plant and whose empirical formula is: $C_{16}H_{10}N_2O_2$; its structure is:

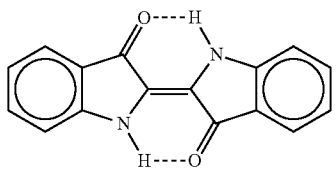

It is possible to use, mixed with indigo, other additional organic dyes from the indigoid family, alone or mixtures thereof, such as indirubin, indigotin, halogen-indigos such as dichloroindigo, dibromoindigo, thioindigos, indigo acetates.

Preferably, when they are present, these additional organic dyes represent 0.01 to 25 wt. %, notably 0.1 to 20 wt. %, or even 0.5 to 13 wt. %, of the 'indigo+additional indigoid dyes' mixture.

Preferably, the organic dye compounds are in solid form at 25° C.; they can however be in liquid form at 25° C.

Advantageously, the organic dye compounds are used as such, i.e. without solvent.

To be able to be incorporated in the tunnels of the fibrous matrix, the organic dye compounds are preferably such that at least two of their dimensions are less than or equal to, respectively, 1.1 nm and 0.57 nm, with any value for the third dimension. Preferably, one of the dimensions is between 1.0 and 1.1 nm, notably between 1.04 and 1.08 nm; and/or another dimension is between 0.25 and 0.45 nm, notably between 0.30 and 0.40 nm.

The organic dye compounds can bear one or more polar functions, notably thiol, which can facilitate their incorporation in the tunnels of the fibrous matrix.

In order to prepare the colorants according to the invention, the inorganic fibrous matrix with tunnels and the organic dye compounds are mixed together, in such a way that said dye compounds are incorporated, at least partially, in the tunnels of the fibrous matrix.

The organic dye compound is present in the colorant in an amount such that the initial weight ratio of organic dye compound (total, therefore including optionals) to inorganic fibrous matrix is greater than or equal to 0.028 (i.e. 2.8%), notably between 0.0285 (2.85%) and 0.20 (20%), better still between 0.029 (2.9%) and 0.15 (15%), or even between 0.03 (3%) and 0.13 (13%), and preferably between 0.032 (3.2%) and 0.08 (8%).

To obtain a particularly homogeneous mixture, a stage of mixing/kneading can be carried out; this can be carried out in a grinding mill notably of the pestle-and-mortar type, or in a concrete mixer.

The optional stage of mixing/kneading preferably is not for the purpose of reducing the size of the fibrous matrix, as the fibrous matrix comprises the dye compounds preferably having a size almost identical to that of the initial fibrous matrix.

The stage of mixing/kneading can be carried out for 10 seconds to 72 hours, notably 1 to 120 minutes, better still 10 to 100 minutes. It is preferably carried out at room temperature (20-30° C.).

The mixture comprising the inorganic fibrous matrix and the organic dye compounds, optionally ground/kneaded, is preferably submitted to thermal treatment at a temperature greater than or equal to 250° C., for a total time greater than or equal to 12 minutes.

The time and the temperature of thermal treatment must be selected in such a way that the organic dye compounds are finally incorporated at least partially in the inorganic fibrous matrix.

Thus, the higher the temperature of thermal treatment, the more the time can be reduced. Conversely, the lower the temperature, the more the thermal treatment time must be increased; this has the aim of obtaining adequate incorporation of the dye compounds in the matrix, and therefore the desired photostability.

The number of stages of thermal treatment can also be taken into account; it is thus possible to carry out said thermal treatment in several stages, notably in two, three or four heating stages. It is possible to heat for a shorter time, and/or at a lower temperature, if the thermal treatment is carried out in several stages.

Thus, the thermal treatment time is preferably greater than or equal to 12 minutes, preferably between 12 and 120 minutes, notably between 15 and 90 minutes, or even between 20 and 75 minutes; this time is the total thermal treatment time, i.e. the sum of the thermal treatment times, when there are several heating stages.

As for the temperature of thermal treatment, it is, for each stage, greater than or equal to 250° C., preferably between 250° C. and 600° C., notably between 260° C. and 575° C., or even between 270° C. and 550° C., preferably between 300° C. and 500° C.

In a first preferred embodiment of the invention, the thermal treatment can be carried out in a single stage, at a temperature greater than or equal to 320° C., notably between 320° C. and 600° C., preferably between 340° C. and 550° C., for a time greater than or equal to 15 minutes, notably between 15 and 45 minutes, preferably between 18 and 40 minutes.

In a second preferred embodiment of the invention, the thermal treatment can be carried out in a single stage, at a temperature greater than or equal to 250° C., notably between 250° C. and 320° C., preferably between 260° C. and 300° C., for a time greater than or equal to 45 minutes, notably between 45 and 120 minutes, preferably between 50 and 90 minutes.

In a third preferred embodiment of the invention, the thermal treatment can be carried out in two stages, the first stage being carried out at a temperature greater than or equal to 250° C., notably between 250° C. and 320° C., preferably between 260° C. and 300° C., for a time greater than or equal to 10 minutes, notably between 10 and 120 minutes, preferably between 15 and 90 minutes;
the second stage being carried out at a temperature greater than or equal to 250° C., notably between 250° C. and 350° C., preferably between 270° C. and 320° C., for a time greater than or equal to 5 minutes, notably between 5 and 90 minutes, preferably between 10 and 60 minutes.

Preferably, the temperature of the second stage is higher than that of the first stage, notably higher than at least 10° C.

In a fourth preferred embodiment of the invention, the thermal treatment can be carried out in three stages, each stage being carried out at a temperature greater than or equal to 320° C., notably between 320° C. and 600° C., preferably between 340° C. and 550° C., for a time greater than or equal to 4 minutes, notably between 4 and 40 minutes, preferably between 5 and 30 minutes.

The thermal treatment can be carried out by a person skilled in the art in any type of furnace; preferably the mixture is fed into the furnace previously heated to the desired treatment temperature.

When the thermal treatment is carried out in several stages, the mixture is preferably left to cool to room temperature (25° C.), in the open air, between each stage.

It was found that the thermal treatment according to the invention leads to colorants that are very photostable, which therefore keep their colour and their colouring power even after exposure to the light for a long period.

Moreover, the colorants according to the invention display very slight, or even nonexistent, salting out on heating, the organic dye compounds being stabilized and immobilized long-term in the inorganic fibrous matrix.

The colorants according to the invention can be used advantageously in the cosmetics field.

They can be present in cosmetic compositions in a proportion from 0.1 to 70 wt. %, notably 0.5 to 50 wt. %, or even 1 to 40 wt. %, preferably 5 to 35 wt. %, relative to the total weight of the cosmetic composition.

Said cosmetic composition further comprises a cosmetically acceptable medium, i.e. a medium compatible with cutaneous tissues such as the skin of the face or of the body, and keratinous materials such as the hair, eyelashes, eyebrows and nails.

The composition can then comprise, according to the application envisaged, the constituents that are usual for this type of composition.

The composition according to the invention can advantageously comprise a liquid oil phase, which can comprise at least one compound selected from the oils and/or solvents of mineral, animal, vegetable or synthetic origin, carbon-containing, hydrocarbon-containing, fluorinated and/or siliconized, volatile or non-volatile, alone or mixed provided that they form a homogeneous and stable mixture and are compatible with the use envisaged.

'Volatile' means, in the sense of the invention, any compound that is liable to evaporate in contact with keratinous materials, or the lips, in less than an hour, at room temperature (25° C.) and atmospheric pressure (1 atm). Notably, this volatile compound has a non-zero vapour pressure, at room temperature and atmospheric pressure, notably in the range from 0.13 Pa to 40 000 Pa ($10^{-3}$ to 300 mmHg).

Conversely, 'non-volatile' means a compound that remains on keratinous materials or on the lips at room temperature and atmospheric pressure, for at least one hour and notably has a vapour pressure below $10^{-3}$ mmHg (0.13 Pa).

Preferably, the cosmetically acceptable medium of the composition according to the invention can comprise, in a liquid oil phase, at least one oil and/or solvent that can be selected from, alone or mixed:

1/ esters of monocarboxylic acids with monohydric alcohols and polyalcohols; advantageously, said ester is a C12-C15 alkyl benzoate or corresponds to the following formula: $R'_1$—COO—$R'_2$ where:

$R'_1$ represents a linear or branched alkyl radical with 1 to 40 carbon atoms, preferably with 7 to 19 carbon atoms, optionally comprising one or more ethylenic double bonds, optionally substituted and whose hydrocarbon chain can be interrupted by one or more heteroatoms selected from N and O and/or one or more carbonyl functions, and $R'_2$ represents a linear or branched alkyl radical with 1 to 40 carbon atoms, preferably 3 to 30 carbon atoms and better still 3 to 20 carbon atoms, optionally comprising one or more ethylenic double bonds, optionally substituted and whose hydrocarbon chain can be interrupted by one or more heteroatoms selected from N and O and/or one or more carbonyl functions.

"Optionally substituted" means that $R'_1$ and/or $R'_2$ can bear one or more substituents, selected for example from the groups comprising one or more heteroatoms selected from O and/or N, such as amino, amine, alkoxy, hydroxyl.

Examples of groups $R'_1$ are those derived from the, preferably higher, fatty acids selected from the group comprising acetic, propionic, butyric, caproic, caprylic, pelargonic, capric, undecanoic, lauric, myristic, palmitic, stearic, isostearic, arachidic, behenic, oleic, linolenic, linoleic, oleostearic, arachidonic, erucic acids, and mixtures thereof.

Preferably, $R'_1$ is a branched, unsubstituted alkyl group with 4 to 14 carbon atoms, preferably 8 to 10 carbon atoms and $R_2$ is a branched, unsubstituted alkyl group with 5 to 15 carbon atoms, preferably 9 to 11 carbon atoms.

We may mention in particular, preferably, the $C_8$-$C_{48}$ esters, optionally incorporating in their hydrocarbon chain one or more heteroatoms from N and O and/or one or more carbonyl functions; and more particularly purcellin oil (cetostearyl octanoate), isononyl isononanoate, isopropyl myristate, isopropyl palmitate, ethyl-2-hexyl palmitate, octyl-2-dodecyl stearate, octyl-2-dodecyl erucate, isostearyl isostearate, benzoate of $C_{12}$ to $C_{15}$ alcohol, hexyl laurate, diisopropyl adipate; and heptanoates, octanoates, decanoates or ricinoleates of alcohols or of polyalcohols, for example of fatty alcohols such as propylene glycol dioctanoate, as well as isopropyl N-lauroyl sarcosinate (notably Eldew-205SL from Ajinomoto); hydroxylated esters such as isostearyl lactate, diisostearyl malate; and esters of pentaerythritol; branched C8-C16 esters, notably isohexyl neopentanoate.

2/ hydrocarbon vegetable oils with high content of triglycerides constituted of esters of fatty acids and of glycerol whose fatty acids can have chain lengths varying from $C_4$ to $C_{24}$, and the latter can be linear or branched, saturated or unsaturated; said oils are notably wheat germ oil, maize oil, sunflower oil, karite oil, castor oil, sweet almond oil, macadamia oil, apricot oil, soya oil, colza oil, cotton oil, alfalfa oil, poppy oil, Chinese okra oil, sesame oil, cucurbit oil, avocado oil, hazelnut oil, grapeseed oil, blackcurrant seed oil, evening primrose oil, millet oil, barley oil, quinoa oil, olive oil, rye oil, safflower oil, candlenut oil, passionflower oil, musk rose oil, jojoba oil, palm oil, calophyllum oil; or the triglycerides of caprylic/capric acids such as those sold by the company Stearinerie Dubois or those sold under the names "Miglyol 810®", "812®" and "818®" by the company Dynamit Nobel.

3/ alcohols, and notably C6-C32, notably C12-C26, monohydric alcohols, such as oleic alcohol, linoleic alcohol, linolenic alcohol, isostearyl alcohol, 2-hexyldecanol, 2-butyloctanol, 2-undecylpentadecanol and octyldodecanol;

4/ volatile or non-volatile, linear or branched hydrocarbon oils, of synthetic or mineral origin, which can be selected from hydrocarbon oils having from 5 to 100 carbon atoms, and notably petroleum jelly, polydecenes, hydrogenated polyisobutenes such as Parleam, squalane, perhydrosqualene and mixtures thereof.

We may more particularly mention the linear, branched and/or cyclic C5-C48 alkanes, and preferably the branched C8-C16 alkanes such as the C8-C16 isoalkanes of petroleum origin (also called isoparaffins); notably decane, heptane, dodecane, cyclohexane; as well as isododecane, isodecane, isohexadecane.

5/ volatile or non-volatile silicone oils;

As volatile silicone oils, we may mention volatile linear or cyclic silicone oils, notably those having a viscosity of less than 8 centistokes, and notably having from 2 to 10 silicon atoms, said silicones optionally bearing alkyl or alkoxy groups having from 1 to 22 carbon atoms; and in particular octamethylcyclotetrasiloxane, decamethylcyclopentasiloxane, dodecamethylcyclohexasiloxane, heptamethylhexyltrisiloxane, heptamethyloctyltrisiloxane, hexamethyldisiloxane, octamethyltrisiloxane, decamethyltetrasiloxane, dodecamethylpentasiloxane, methylhexyldimethylsiloxane and mixtures thereof.

The non-volatile silicone oils usable according to the invention can be polydimethylsiloxanes (PDMS), polydimethylsiloxanes bearing alkyl or alkoxy groups, pendant and/or at the end of the silicone chain, groups each having from 2 to 24 carbon atoms, phenylated silicones such as phenyltrimethicones, phenyldimethicones, phenyltrimethylsiloxydiphenylsiloxanes, diphenyldimethicones, diphenylmethyldiphenyltrisiloxanes, 2-phenylethyl trimethylsiloxysilicates.

The liquid oil phase can moreover comprise additional oils and/or solvents, which can be selected from, alone or mixed:

fluorinated oils such as perfluoropolyethers, perfluoroalkanes such as perfluorodecalin, perfluorodamantanes, monoesters, diesters and triesters of perfluoroalkylphosphates and fluorinated ester oils;

oils of animal origin;

$C_6$ to $C_{40}$, notably C10-C40, ethers; ethers of propylene glycol that are liquid at room temperature such as propylene glycol monomethylether, propylene glycol monomethylether acetate, dipropylene glycol mono-n-butyl ether;

$C_8$-$C_{32}$ fatty acids, such as oleic acid, linoleic acid, linolenic acid and mixtures thereof;

bifunctional oils, comprising two functions selected from ester and/or amide and comprising 6 to 30 carbon atoms, notably 8 to 28 carbon atoms, better still 10 to 24 carbons, and 4 heteroatoms selected from O and N; preferably the amide and ester functions being in the chain;

ketones that are liquid at room temperature (25° C.) such as methyl ethyl ketone, methyl isobutyl ketone, diisobutyl ketone, isophorone, cyclohexanone, acetone;

aldehydes that are liquid at room temperature such as benzaldehyde, acetaldehyde.

The liquid oil phase can represent 1 to 90 wt. % of the composition, notably from 5 to 75 wt. %, in particular from 10 to 60 wt. %, or even from 25 to 55 wt. %, of the total weight of the composition.

The composition according to the invention can advantageously comprise a thickener, which can in particular be selected from:

silicas, notably hydrophobic, clays such as montmorillonite, modified clays such as bentones for example, stearalkonium bentonite, stearalkonium hectorite, alkylethers of polysaccharides (notably whose alkyl group has from 1 to 24 carbon atoms, preferably from 1 to 10, better still from 1 to 6, and more especially from 1 to 3).

The amount of thickener in the composition according to the invention can range from 0.05 to 40 wt. %, relative to the total weight of the composition, preferably from 0.5 to 20% and better still from 1 to 15 wt. %.

The composition according to the invention can also comprise at least one wax of vegetable, animal, mineral or synthetic origin, or even silicone wax.

We may mention in particular, alone or mixed, hydrocarbon waxes such as beeswax; carnauba wax, candelilla wax, ouricury wax, Japan wax, cork-fibre or sugarcane waxes; paraffin and lignite waxes; microcrystalline waxes; lanolin wax; montan wax; ozokerites; polyethylene waxes; waxes obtained by Fischer-Tropsch synthesis; hydrogenated oils, fatty esters and glycerides that are solid at 25° C. It is also possible to use silicone waxes, among which we may mention alkyl, alkoxy and/or esters of polymethylsiloxane.

The amount of wax in the composition according to the invention can range from 0.1 to 70 wt. %, relative to the total weight of the composition, preferably from 1 to 40 wt. %, and better still from 5 to 30 wt. %.

The composition according to the invention can also comprise one or more additional colorants, which can be selected from pulverulent compounds such as pigments, fillers, nacres and glitter, and/or fat-soluble or water-soluble dyes.

The colorants, notably pulverulent, can be present in the composition at a content from 0.01 to 50 wt. %, relative to the weight of the composition, preferably from 0.1 to 40 wt. %, or even from 1 to 30 wt. %.

"Pigments" are to be understood as particles of any shape, white or coloured, mineral or organic, insoluble in the physiological environment, intended for colouring the composition.

"Nacres" are to be understood as iridescent particles of any shape, notably produced in the shell of certain molluscs, or else synthesized.

Pigments can be white or coloured, mineral and/or organic, with or without interference effects. We may mention, among the mineral pigments, titanium dioxide, optionally surface-treated, oxides of zirconium or of cerium, as well as oxides of iron or of chromium, manganese violet, ultramarine blue, chromium hydrate and ferric blue. Among organic pigments, we may mention carbon black, D & C type pigments, and lakes based on carmine, and barium, strontium, calcium, aluminium lakes.

The nacreous pigments can be selected from the white nacreous pigments such as mica covered with titanium, or with bismuth oxychloride, the coloured nacreous pigments such as titanium mica with iron oxides, titanium mica notably with ferric blue or chromium oxide, titanium mica with an organic pigment of the aforementioned type as well as nacreous pigments based on bismuth oxychloride.

The fillers can be mineral or organic, lamellar or spherical. We may mention talc, mica, silica, kaolin, powders of Nylon and of polyethylene, of poly-β-alanine and of polyethylene, Teflon, lauroyl-lysine, starch, boron nitride, powders of tetrafluoroethylene polymers, hollow microspheres such as Expancel (Nobel Industrie), polytrap (Dow Corning) and microbeads of silicone resin (Tospearls from Toshiba, for example), precipitated calcium carbonate, magnesium carbonate and hydrocarbonate, hydroxyapatite, hollow silica microspheres (SILICA BEADS from MAPRECOS), glass or ceramic microcapsules, metal soaps derived from organic carboxylic acids having from 8 to 22 carbon atoms, preferably 12 to 18 carbon atoms, for example zinc, magnesium or lithium stearate, zinc laurate, magnesium myristate.

The fat-soluble dyes are for example Sudan red, D&C Red 17, D&C Green 6, β-carotene, soya oil, Sudan brown, D&C Yellow 11, D&C Violet 2, D&C orange 5, quinoline yellow. They can represent 0.01 to 20% of the weight of the composition and better still from 0.1 to 6%.

The water-soluble dyes are for example beetroot juice, methylene blue and can represent 0.01 to 6% of the total weight of the composition.

The composition can comprise, moreover, other ingredients commonly used in cosmetic compositions. Such ingredients can be selected from antioxidants, perfumes, essential oils, preservatives, cosmetic actives, hydrating agents, vitamins, ceramides, sun filters, surfactants, spreading agents, wetting agents, dispersants, antifoaming agents, neutralizing agents, stabilizers, polymers and notably fat-soluble film-forming polymers, and mixtures thereof.

Of course, a person skilled in the art will take care to select this or these optional additional compounds, and/or their amount, in such a way that the advantageous properties of the composition for use according to the invention are not, or substantially not, adversely affected by the addition envisaged.

The compositions according to the invention can be in any form that is acceptable and usual for a cosmetic or pharmaceutical composition.

They can therefore be in the form of a suspension, a dispersion notably of oil in water owing to vesicles; an organic or oily solution optionally thickened or even jellified; an oil-in-water, water-in-oil, or multiple emulsion; a gel or a mousse; an oily or emulsified gel; a dispersion of vesicles, notably of lipid vesicles; a biphase or multiphase lotion; a spray; a lotion, a cream, an ointment, a soft paste, an unguent, a cast or moulded solid and notably as a stick or in a dish, or a compacted solid.

A person skilled in the art will be able to select the appropriate dosage form, as well as its method of preparation, on the basis of his general knowledge, taking into account on the one hand the nature of the constituents used, notably their solubility in the substrate, and on the other hand the application envisaged for the composition.

The compositions according to the invention can be used for the care or make-up of keratinous materials such as the hair, the skin, the eyelashes, the eyebrows, the nails, the lips, the scalp and more particularly for making up the lips, eyelashes and/or the face.

They can therefore be in the form of a product for care and/or make-up of the skin of the body or of the face, the lips, eyelashes, eyebrows, hair, scalp or the nails; a tanning or self-tanning product; a hair product notably for colouring, conditioning and/or of care of the hair; they are advantageously in the form of a make-up composition, notably mascara, lipstick, blusher, eye-shadow, foundation.

The colorants according to the invention find quite preferable application in make-up compositions of the eye-shadow or blusher type.

In this embodiment, the composition according to the invention preferably comprises a cosmetically acceptable anhydrous medium, i.e. an anhydrous medium compatible with the skin of the eyelids. This anhydrous medium forms a continuous phase. "Anhydrous medium" means a medium comprising less than 5% water, and better still less than 1% water.

This anhydrous medium can comprise in particular at least one oil, which is preferably selected from the oils of mineral, animal, vegetable or synthetic origin, hydrocarbon and/or silicone oils, notably as mentioned above, and mixtures thereof. The oil can be present in the composition according to the invention at a content in the range from 0.1 to 60 wt. %, relative to the total weight of the composition, preferably in the range from 1 to 40 wt. %, and more preferably in the range from 5 to 25 wt. %.

This medium can also comprise additional fats other than oils, such as the waxes notably mentioned above, pastes or gums. As pasty fats, we may mention fats having a melting point in the range from 25 to 45° C. and/or a viscosity at 40° C. in the range from 0.1 to 40 Pa·s measured with the Contraves TV instrument equipped with an MS-r3 or Ms-r4 spindle rotating at 60 Hz. As examples of pasty fats, we may mention the lanolins and the lanolin derivatives such as the acetylated lanolins or the propoxylated lanolins, and mixtures thereof; esters of acids or of fatty alcohols, notably those having 20 to 65 carbon atoms such as triisostearyl or cetyl citrate, arachidyl propionate, vinyl polylaurate, cholesterol esters such as triglycerides of vegetable origin such as hydrogenated vegetable oils, viscous polyesters such as poly(12-hydroxystearic acid) and mixtures thereof. As triglycerides of vegetable origin, it is possible to use derivatives of hydrogenated castor oil, such as "THIXINR" from Rheox. We may also mention siliconized pasty fats such as polydimethylsiloxanes (PDMS) having pendant chains of alkyl or alkoxy type having from 8 to 24 carbon atoms, and a melting point of 20-55° C., such as stearyl dimethicones; and mixtures thereof. As gums, it is possible to use silicone gums (dimethiconols) for example the dimethiconol/cyclopentasiloxane mixture. The additional fat can be present at a content from 0.1 to 30 wt. %, relative to the total weight of the composition, and preferably from 1 to 15 wt. %.

The composition can comprise an emulsifier. In particular, a water-soluble emulsifier is used, in particular having an HLB (hydrophilic-lipophilic balance) greater than or equal to 10 at 25° C. The emulsifier can be selected from the amphoteric, anionic, cationic or non-ionic emulsifiers, and mixtures thereof. As amphoteric emulsifiers, we may mention the N-acyl-amino acids such as the N-alkyl-amino acetates and disodium cocoamphodiacetate and the oxides of amines such as stearamine oxide. As anionic emulsifiers, we may mention the acylglutamates such as "disodium hydrogenated tallow glutamate" (AMISOFT HS-21® marketed by the company Ajinomoto); the carboxylic acids and their salts such as sodium stearate; the phosphoric esters and their salts such as "DEA oleth-10 phosphate"; the sulphosuccinates such as "Disodium PEG-5 citrate lauryl sulphosuccinate" and "Disodium ricinoleamido MEA sulphosuccinate"; the alkyl ether sulphates such as sodium lauryl ether sulphate; the sulphosuccinates; the isethionates. As cationic emulsifiers, we may mention the alkyl-imidazolidiniums such as isostearyl-ethylimidonium etho-sulphate; ammonium salts such as N,N,N-trimethyl-1-docosanaminium chloride (Behentrimonium chloride). As non-ionic emulsifiers, we may mention the esters and ethers of monosaccharides such as sucrose stearate, sucrose cocoate, and the mixture of sorbitan stearate and sucrose cocoate marketed by the company ICI under the name Arlatone 2121; the esters of fatty acids (notably of C8-C24 acid, and preferably of C16-C22 acid) and of polyol, notably of glycerol or of sorbitol, such as glyceryl stearate, polyglyceryl-2 stearate, sorbitan tristearate, glyceryl ricinoleate; the glycerol ethers; the ethoxylated and/or propoxylated ethers (which can have from 1 to 150 ethoxylated and/or propoxylated groups) of fatty alcohols (notably of C8-C24, and preferably C12-C18, alcohol) such as the ethoxylated, propoxylated ether of lauric alcohol with 25 ethoxylated groups and 25 propoxylated groups (CTFA name "PPG-25 laureth-25") and the ethoxylated ether of the mixture of C12-C15 fatty alcohols having 7 ethoxylated groups (CTFA name "C12-15 Pareth-7"); the esters of fatty acid (notably of C8-C24, and preferably C16-C22, acid) and of polyethylene glycol (which can comprise from 1 to 150 ethylene glycol units) such as PEG-50 stearate and PEG-40 stearate; the copolymers of propylene oxide and of ethylene oxide such as those sold under the names SYNPERONIC by UNIQEMA. As silicone emulsifiers, we may mention the dimethicone copolyols, such as those sold under the names "DC2-5695" and "Q2-5220"

by the company Dow Corning, the mixture of cyclomethicone/dimethicone copolyol sold under the name "Q2-3225C" by the company Dow Corning, the dimethicone copolyol phosphates such as that sold under the name PECOSIL PS 100 by the company PHOENIX CHEMICAL. As silicone emulsifier, it is also possible to use a dimethicone copolyol benzoate, i.e. a partial ester of benzoic acid and dimethicone copolyol, the latter being a dimethylpolysiloxane polymer bearing side chains of polyoxyethylene and/or of polyoxypropylene. As dimethicone copolyol benzoate, it is possible to use those sold under the name FINSOLV by the company FINETEX. The emulsifier can be present in the composition according to the invention at a content from 0.1 to 30 wt. %, relative to the total weight of the composition, preferably from 0.5 to 20 wt. %, and more preferably from 1 to 10 wt. %.

Preferably, the composition according to the invention comprises an additional colorant, which can be selected from the pulverulent colorants such as pigments, nacres, glitter or else water-soluble colorants, usually employed in cosmetic compositions and such as described above, and mixtures thereof. The additional colorant can be present in the composition according to the invention at a content from 0.1 to 50 wt. %, relative to the total weight of the composition, preferably from 1 to 40 wt. %, and more preferably from 10 to 35 wt. %.

The composition according to the invention can comprise, moreover, at least one glycol, to permit good wetting of the pigments, i.e. facilitate their application and their homogeneous dispersion (absence of agglomerates) in the aqueous medium during preparation of the composition, then promote redispersion of the pigments during contacting of the solid eye-shadow with an aqueous phase before application on the eyelids. The glycol permits good wetting of the skin, facilitating spreading of the composition on the eyelid. In the present application, glycol means a diol comprising from 2 to 8, and preferably from 2 to 4, carbon atoms. The glycol can be selected from propylene glycol, ethylene glycol, 1,3-butylene glycol, dipropylene glycol, and mixtures thereof. The glycol can be present in the composition at a content from 0.1 to 40 wt. %, relative to the total weight of the composition, and preferably from 5 to 20 wt. %.

The composition according to the invention can comprise fillers, which can be selected from talc, used in the form of particles generally smaller than 40 microns; micas, which are aluminosilicates of varied compositions in the form of scales having dimensions from 2 to 200 microns, and a thickness between 0.1 and 5 microns, and said micas can be of natural origin such as muscovite, margarite, roscoelite, lipidolite, biotite or of synthetic origin; starch in particular rice starch; kaolin, which can be in the form of particles of isotropic shape having dimensions generally smaller than 30 microns; the oxides of zinc and of titanium generally used in the form of particles having dimensions not exceeding a few microns; calcium carbonate, magnesium carbonate or hydrocarbonate; microcrystalline cellulose; silica; powders of synthetic polymers such as polyethylene, polyesters (polyethylene isophthalate or terephthalate), polyamides such as those sold under the trade name of "Nylon" or "Teflon" and the silicone powders.

According to an advantageous embodiment, the eye-shadow according to the invention comprises:
a solid fat phase, which comprises at least one wax; preferably the solid fat phase is present at a content from 1 to 30 wt. %, notably from 2 to 20 wt. % relative to the total weight of the composition.
a liquid oil phase at a content less than or equal to 10 wt. % relative to the total weight of the composition, preferably less than or equal to 7 wt. %, preferably less than or equal to 5 wt. %, better less than or equal to 3 wt. % and better still less than or equal to 3 wt. %; even better still the eye-shadow composition is free from liquid oil phase.

at least one filler, which can be organic or mineral, of spherical or lamellar form, and can be present at a content from 0.1 to 50 wt. % relative to the total weight of the composition, preferably in the range from 1 to 40 wt. %.

Preferably, the eye-shadow is anhydrous, i.e. is a composition containing less than 2 wt. % of water (added water), or even less than 0.5 of water, notably less than 0.2% of water, and the water that may be present is not added during preparation of the composition but corresponds to the residual water supplied by the ingredients of the mixture.

The invention further relates to a method of cosmetic treatment of keratinous materials, notably of the skin of the body or of the face, lips, nails, hair and/or eyelashes, comprising the application of a cosmetic composition such as defined previously on said materials.

This method according to the invention notably permits the making up of said keratinous materials, in particular of the lips, face, eyelids and/or cheeks, by application of a composition of lipstick, of eye-shadow or blusher, or of foundation, according to the invention.

The invention is illustrated in more detail in the following examples of application.

EXAMPLE 1

(x) g of indigo (synthetic indigo; content of crystallized indigo: 95%) is mixed dry with 25 g of sepiolite (Tolsa S9 grade, $(Si)_{12}(Mg)_8(O)_{30}(OH)_4(OH_2)_4$, $8H_2O$, dimensions of the tunnels 1.06×0.37 nm).

If necessary, the mixture is mixed/ground for (y) minutes, in a grinding mill of the pestle-and-mortar type, then the mixture is submitted to thermal treatment in a muffle furnace with a volume of 8000 $cm^3$, for a time (t) at a temperature (T). Heating is carried out under ambient air, and the mixture is put in the furnace previously heated to the required temperature.

If necessary, the thermal treatment can be carried out in several stages, with a phase of cooling in the open air to room temperature (25° C.) between each stage.

The colorant thus obtained, which is in the form of powder, is then left to cool to 25° C.

The colorimetric coordinates of said colorant are determined as follows: compacted powders are prepared under a pressure of 100 bar, in a dish of type FAP247; the amount of colorant is adjusted so as to fill the dish completely. The dish is covered with a glass slide and then the colorimetric coordinates are measured in SCE mode (specular excluded) under D65 illuminant (daylight).

The results obtained are shown in the following table, in which:

(x) indicates, in grams, the initial amount of indigo added to the sepiolite

% indicates the indigo/sepiolite weight ratio (×100)

(y) indicates, in minutes, the mixing/grinding time (T) indicates, in ° C., the temperature of thermal treatment (t) indicates, in minutes, the duration of thermal treatment.

(i) a single heating stage:

|   | (x)   | %   | (y) | (T) | (t) | L*    | a*    | b*     | C*   | h*     |
|---|-------|-----|-----|-----|-----|-------|-------|--------|------|--------|
| A | 0.725 | 2.9 | 15  | 350 | 30  | 20.63 | −5.48 | −7.72  | 9.47 | 234.64 |
| B | 0.725 | 2.9 | 15  | 500 | 20  | 20.12 | −0.38 | −1.59  | 1.64 | 256.61 |
| C | 2.42  | 9.7 | 15  | 500 | 30  | 15.06 | −0.27 | −0.34  | 0.44 | 232.43 |
| D | 0.725 | 2.9 | 90  | 260 | 60  | 27.04 | −8.84 | −15.67 | 18   | 240.57 |

(ii) two heating stages (with cooling to 25° C. between each stage):

|   | (x)   | %   | (y) | thermal treatment | L* | a* | b* | C* | h* |
|---|-------|-----|-----|-------------------|-----|-----|-----|-----|-----|
| E | 0.725 | 2.9 | 15  | 18 min at 260° C. then 10 min at 280° C. | 29.14 | −7.12 | −23.19 | 24.26 | 252.93 |
| F | 0.725 | 2.9 | 60  | 60 min at 260° C. then 40 min at 300° C. | 26.34 | −8.08 | −10.46 | 13.21 | 232.32 |
| G | 0.725 | 2.9 | 60  | 60 min at 260° C. then 10 min at 300° C. | 28.05 | −9.99 | −14 | 17.2 | 234.48 |

(iii) three heating stages (with cooling to 25° C. between each stage):

|   | (x) | % | (y) | thermal treatment | L* | a* | b* | C* | h* |
|---|-----|---|-----|-------------------|-----|-----|-----|-----|-----|
| H | 2.42 | 9.7 | 15 | 400° C. for 18 min then 5 min then 16 min | 14.88 | −1.87 | −5.05 | 5.38 | 249.65 |

Colorants are obtained in the form of powder, and have various shades of blue, depending on the heating temperature and time.

It is generally found that the higher the temperature of thermal treatment and/or the longer the treatment time, the darker the shade obtained (decrease of L* and C*).

It is also found that the higher the proportion of indigo (colorants C and H), the darker the shade (decrease of L*).

The thermal treatment of the indigo/clay mixture can be applied either in a single stage, or in several stages: it is then called annealing. Annealing has an influence on the shade obtained, as illustrated by experiments C and H: the annealed sample H is more saturated and more blue than the unannealed sample C.

EXAMPLE 2

Exactly as in example 1, 0.725 g of indigo (i.e. 2.9%) and 0.15 g of indirubin are mixed dry with 25 g of sepiolite; the mixture is mixed/ground for 15 minutes in a grinding mill of the pestle-and-mortar type, then submitted to thermal treatment in a muffle furnace, at 260° C. for 18 minutes, left to cool to 25° C., then submitted to thermal treatment again at 280° C. for 10 minutes, obtaining a colorant in the form of blue powder, which is left to cool to 25° C.

As in example 1, the colorimetric coordinates of said colorant are determined:

|      | L*    | a*    | b*     | C*    | h*     |
|------|-------|-------|--------|-------|--------|
| Ex 2 | 26.85 | −4.82 | −22.44 | 22.95 | 257.87 |

In comparison with sample E in example 1, the colorant in example 2 has a more pronounced red hue, which is reflected in an increase of the hue angle h* and of the red component a*.

EXAMPLE 3

Exactly as in example 1, 0.725 g of indigo (i.e. 2.9%) is mixed dry with 25 g of attapulgite (or palygorskite, Absonet A special from Tolsa); the mixture is mixed/ground for 15 minutes, in a grinding mill of the pestle-and-mortar type, then submitted to thermal treatment at 260° C. for 60 minutes, obtaining a colorant in the form of blue powder, which is left to cool to 25° C.

As in example 1, the colorimetric coordinates of said colorant are determined:

|      | L*    | a*    | b*     | C*   | h*     |
|------|-------|-------|--------|------|--------|
| Ex 3 | 27.67 | −7.85 | −15.19 | 17.1 | 242.69 |

EXAMPLE 4

The photostability of the colorants according to the invention, as well as of colorants outside the scope of the invention (time or temperature of thermal treatment outside the scope of the invention), prepared according to the method of example 1, is determined.

1/ Comparative Samples Prepared (i) a single heating stage:

|    | (x)   | %    | (y) | (T)             | (t)          |
|----|-------|------|-----|-----------------|--------------|
| A' | 0.725 | 2.9  | 60  | 0 (no heating)  | 0            |
| B' | 0.242 | 0.97 | 15  | 550             | 1.75 (105 s) |
| C' | 0.725 | 2.9  | 15  | 255             | 24           |
| D' | 0.242 | 0.97 | 15  | 350             | 24           |

(ii) several heating stages (with cooling to 25° C. between each stage):

|    | (x)   | %    | (y) | thermal treatment |
|----|-------|------|-----|-------------------|
| E' | 0.121 | 0.48 | 15  | 2 stages: 18 min at 260° C. then 3 min at 300° C. |

-continued

|   | (x)   | %    | (y) | thermal treatment                                           |
|---|-------|------|-----|-------------------------------------------------------------|
| F'| 0.242 | 0.97 | 60  | 2 stages: 60 min at 260° C. then 10 min at 300° C.          |
| G'| 0.483 | 1.93 | 15  | 2 stages: 18 min at 260° C. then 10 min at 280° C.          |
| H'| 0.242 | 0.97 | 15  | 4 stages: 12 min then 4 min then 4 min then 4 min, at 350° C. |

The photostability is determined as follows:

The colorant is compacted in two separate dishes under a pressure of 100 bar.

One of the dishes is kept away from the light and is used as colour reference.

The other dish is submitted to the Sun Test for 24 hours.

After the Sun Test, 3 persons compare the two samples visually, in a light booth under a D65 illuminant.

A note 'yes' signifies that the colour difference of the sample before and after irradiation is considered by the 3 testers as imperceptible (or barely perceptible) to the eye. In this case, the sample is regarded as photostable.

A note 'no' signifies that the colour difference of the sample before and after irradiation is perceptible to the eye for at least one of the testers. The sample is regarded as not photostable.

The results obtained are shown in the following table, which also indicates whether, according to the NMR spectra, the indigo is or is not inside the tunnels in the clay (only 4 samples tested in NMR):

|    | Thermal treatment                                              | Indigo incorporated | Photostability |
|----|----------------------------------------------------------------|---------------------|----------------|
| A  | 30 min at 350° C.                                              | Yes                 | yes            |
| B  | 20 min at 500° C.                                              | Yes                 | yes            |
| C  | 30 min at 500° C.                                              |                     | yes            |
| D  | 60 min at 260° C.                                              | Yes                 | yes            |
| E  | 18 min at 260° C. then 10 min at 280° C.                       |                     | yes            |
| F  | 60 min at 260° C. then 40 min at 300° C.                       |                     | yes            |
| G  | 60 min at 260° C. then 10 min at 300° C.                       |                     | yes            |
| H  | 18 min at 400° C., then 5 min at 400° C., then 16 min at 400° C. |                   | yes            |
| A' | no heating                                                     | No                  | No             |
| B' | 105 seconds at 550° C.                                         |                     | No             |
| C' | 24 minutes at 255° C.                                          |                     | No             |
| D' | 24 minutes at 350° C.                                          |                     | No             |
| E' | 18 min at 260° C. then 3 min at 300° C.                        |                     | No             |
| F' | 60 min at 260° C. then 10 min at 300° C.                       |                     | No             |
| G' | 18 min at 260° C. then 10 min at 280° C.                       |                     | No             |
| H' | 4 stages at 350° C.: 12 min then 4 min then 4 min then 4 min   |                     | No             |

The colorants prepared in examples 2 and 3 are also judged 'photostable'.

It is therefore found that colorants comprising 2% or less of indigo are not satisfactory.

Moreover, even for colorants comprising at least 2.8 wt. % of indigo, it is necessary to find a compromise between the temperature of the thermal treatment and the duration of said treatment.

If the temperature is moderate, it is preferable to have a long treatment time (notably at least 45 minutes) whereas if the temperature is high (notably at least 320° C.), a shorter time (for example 15 minutes) may be sufficient.

EXAMPLE 5

A cosmetic composition of the lipstick type is prepared, comprising (wt. %):
  5% of pigment D
  15% of polyethylene wax
  5% octyldodecanol
  75% Parleam

EXAMPLE 6

A cosmetic composition of the lipstick type is prepared, comprising (wt. %):
  1% of pigment E
  4% of lithol red B
  15% of polyethylene wax
  5% octyldodecanol
  75% Parleam

EXAMPLE 7

A cosmetic composition of mascara is prepared, comprising (wt. %):

| Waxes (carnauba, candelilla, rice bran, vegetable) | 24%        |
|----------------------------------------------------|------------|
| Stearic acid                                       | 5.5%       |
| Hydroxyethyl Cellulose                             | 0.2%       |
| Gum Arabic                                         | 1.5%       |
| Triethanolamine                                    | 2.4%       |
| PEG/PPG-17/18 Dimethicone                          | 0.2%       |
| Polyvinyl Alcohol                                  | 0.2%       |
| Pigment A                                          | 8%         |
| Preservative                                       | qs         |
| Water                                              | q.s.f. 100% |

EXAMPLE 8

A cosmetic composition of eye-shadow is prepared, comprising (wt. %):

| Pigment D                              | 10%         |
|----------------------------------------|-------------|
| DUOCROME BG                            | 20%         |
| Magnesium stearate                     | 2%          |
| Phenyltrimethicone/triisostearin (50/50)| 6%         |
| Talc                                   | q.s.f. 100% |

EXAMPLE 9

A cosmetic composition of styling gel is prepared, comprising (wt. %):

| pigment D                                | 1%          |
| Hydroxypropyl guar (Jaguar HP 105 from RHODIA) | 4%    |
| water                                    | q.s.f. 100% |

The invention claimed is:

1. A cosmetic composition, comprising:
 a cosmetically acceptable medium;
 at least one colorant comprising an inorganic fibrous matrix with tunnels; and
 at least one organic dye compound incorporated at least partially in the tunnels;
 wherein
 at least 30 wt % of the total amount of organic dye is included in the channels of the fibrous matrix,
 the organic dye compound is an indigoid, and
 a weight ratio of organic dye compound to inorganic fibrous matrix is greater than or equal to 0.028, wherein the inorganic fibrous matrix and the organic dye compounds are submitted to a thermal treatment
 (1) carried out in a single stage process at a temperature greater than or equal to 320° C. for a total time greater than or equal to 15 minutes; or
 (2) carried out in a single stage process at a temperature greater than or equal to 250° C. for a total time greater than or equal to 45 minutes; or
 (3) carried out in a two stage process wherein the first stage is carried out at a temperature greater than or equal to 250° C. for a total time greater than or equal to 10 minutes and the second stage is carried out at a temperature greater than or equal to 250° C. for a total time greater than or equal to 5 minutes; or
 (4) carried out in three stages each stage being carried out at a temperature greater than or equal to 320° C. for a total time greater than or equal to 4 minutes.

2. The composition according to claim 1, wherein the inorganic fibrous matrix with tunnels is a fibrous sepiolite or palygorskite clay.

3. The composition according to claim 2, wherein the inorganic fibrous matrix with tunnels is a sepiolite.

4. The composition according to claim 1, wherein the organic dye compound is indigo, or a mixture of indigo and at least one additional organic dye from the indigoid family, selected from the group consisting of indirubin, indigotin, a halogeno-indigo, a thioindigo, and an indigo acetate.

5. The composition according to claim 1, wherein at least two dimensions of the organic dye compounds are less than or equal to, respectively, 1.1 nm and 0.57 nm, with the third dimension having any value.

6. The composition according to claim 1, wherein the weight ratio of organic dye compound to inorganic fibrous matrix is between 0.0285 and 0.20.

7. The composition according to claim 1, wherein the organic dye compounds and the inorganic fibrous matrix are submitted to a stage of mixing/kneading, for 10 seconds to 72 hours.

8. The composition according to claim 1, wherein a content of the colorants is 0.1 to 70 wt. % relative to the total weight of the cosmetic composition.

9. The composition according to claim 1, wherein the cosmetically acceptable medium comprises at least one compound selected from the group consisting of oils, solvents of mineral, animal, vegetable or synthetic origin, carbon-containing oils, hydrocarbon oils, fluorinated oils, volatile or non-volatile silicone oils; thickeners; waxes of vegetable, animal, mineral or synthetic origin, silicone waxes; pigments, fillers, nacres and glitter, fat-soluble or water-soluble dyes; antioxidants, perfumes, essential oils, preservatives, cosmetic actives, hydrating agents, vitamins, ceramides, sun filters, surfactants, spreading agents, wetting agents, dispersants, antifoaming agents, neutralizing agents, stabilizers, polymers and notably film-forming fat-soluble polymers, and mixtures thereof.

10. A product selected from the group consisting of a care and/or make-up of the skin of the body or of the face, lips, eyelashes, eyebrows, hair, scalp or of the nails; a tanning or self-tanning product; a hair product for coloring, conditioning or care of the hair comprising the composition according to claim 1.

11. A mascara, lipstick, blusher, eye-shadow, or foundation comprising the composition according to claim 1.

12. A method for cosmetic treatment of keratinous materials, comprising: applying the cosmetic composition according to claim 1 to the keratinous fiber.

13. A method for making up the lips, face, eyelids and/or cheeks, comprising: applying the cosmetic composition of lipstick, of eye-shadow or blusher, or of foundation, according to claim 11 to the lips, face, eyelids and/or cheeks.

14. The composition according to claim 1, wherein at least two dimensions of the organic dye compound are from 1.1 nm to 0.57 nm.

15. The composition according to claim 1, wherein the inorganic fibrous matrix and the organic dye compounds are submitted to a thermal treatment carried out in a single stage process at a temperature greater than or equal to 320° C. for a total time greater than or equal to 15 minutes.

16. The composition according to claim 1, wherein the inorganic fibrous matrix and the organic dye compounds are submitted to a thermal treatment carried out in a single stage process at a temperature greater than or equal to 250° C. for a total time greater than or equal to 45 minutes.

17. The composition according to claim 1, wherein the inorganic fibrous matrix and the organic dye compounds are submitted to a thermal treatment carried out in a two stage process wherein the first stage is carried out at a temperature greater than or equal to 250° C. for a total time greater than or equal to 10 minutes and the second stage is carried out at a temperature greater than or equal to 250° C. for a total time greater than or equal to 5 minutes.

18. The composition according to claim 1, wherein the inorganic fibrous matrix and the organic dye compounds are submitted to a thermal treatment carried out in three stages each stage being carried out at a temperature greater than or equal to 320° C. for a total time greater than or equal to 4 minutes.

* * * * *

UNITED STATES PATENT AND TRADEMARK OFFICE
CERTIFICATE OF CORRECTION

| | | |
|---|---|---|
| PATENT NO. | : 8,685,419 B2 | Page 1 of 1 |
| APPLICATION NO. | : 12/809175 | |
| DATED | : April 1, 2014 | |
| INVENTOR(S) | : Ivan Rodriguez et al. | |

It is certified that error appears in the above-identified patent and that said Letters Patent is hereby corrected as shown below:

In the Claims:

Column 17, Line 17, "320°C." should read --320°C--
Column 17, Line 20, "250°C." should read --250°C--
Column 17, Line 24, "250°C." should read --250°C--
Column 17, Line 26, "250°C." should read --250°C--
Column 17, Line 29, "320°C." should read --320°C--
Column 18, Line 34, "320°C." should read --320°C--
Column 18, Line 40, "250°C." should read --250°C--
Column 18, Line 46, "250°C." should read --250°C--
Column 18, Line 48, "250°C." should read --250°C--
Column 18, Line 54, "320°C." should read --320°C--

Signed and Sealed this
Seventeenth Day of June, 2014

Michelle K. Lee
*Deputy Director of the United States Patent and Trademark Office*